United States Patent [19]

Wang et al.

[11] Patent Number: 5,670,508
[45] Date of Patent: Sep. 23, 1997

[54] 2-AMINO-6-ALKYL-5-(4-SUBSTITUTED-1-PIPERAZINYL) PYRIMIDIN-4-ONES, THE PREPARATION AND USE THEREOF

[75] Inventors: Hui-Po Wang; Tung-Shing Bai, both of Taipei, Taiwan

[73] Assignee: National Science Council, Taipei, Taiwan

[21] Appl. No.: 548,211

[22] Filed: Oct. 25, 1995

[51] Int. Cl.$^6$ ..................... A61K 31/535; C07D 403/02
[52] U.S. Cl. ........................................ 514/272; 544/295
[58] Field of Search ........................... 544/295; 514/272

[56] References Cited

PUBLICATIONS

Moran et al., Chemical Abstracts 112:91222, 1989.
Baldwin et al., "Structural Features of 5,10–Dideaza–5,6,7,8–tetrahydrofolate the Determine Inhibition of Mammalian Glycinamide Ribonucleotide Formyltransferase", Biochemistry 30:1997–2006, 1991.
Dixon et al., "A Novel cDNA Restores Reduced Folate Carrier Activity and Methotrexate Sensitivity to Transport Deficient Cells", The Journal of Biological Chemistry 269:17–20, 1994.
Hodson et al., "Thienyl and Thiazolyl Acyclic Analogues of 5–Deazatetrahydrofolic Acid", J. Med. Chem. 37:2112–2115, 1994.
Kovacs et al., "Potent Antipneumocystis and Antitoxoplasma Activities of Piritrexim, a Lipid–Soluble Antifolate", Antimicrobial Agents and Chemotherapy 32:430–433, 1988.
Matherly et al., "Characterization of Transport–mediated Methotrexate Resistance in Human Tumor Cells with Antibodies to the Membrane . . . ", The Journal of Biological Chemistry 267:23253–23260, 1992.
Shih et al., "Synthesis and Biological Activity of Acyclic Analogues of 5,10–Dideaza–5,6,7,8–tetrahydrofolic Acid", J. Med. Chem 35:1109–1116, 1992.
Wang et al., "Novel Open–Ring Analogues of $N^5$, $N^{10}$–Methylenetetrahydrofolic Acid With Selective Activity Against Brain Tumor", Bioorganic & Medicinal Chemistry Letters 5:1909–1912, 1995.
Werbel et al., "In Vivo and In Vitro Evaluation of 5–[4–(Substituted Aryl)–1–Piperazinyl]–6–. . . ", Chemistry and Biology of Pteridines 69–71, 1986.

Primary Examiner—Matthew V. Grumbling
Attorney, Agent, or Firm—Fish & Richardson P.C.

[57] ABSTRACT

A series of 2-amino-6-alkyl-5-(4-substituted-1-piperazinyl) pyrimidin-4-ones that have selective cytotoxicity on human CNS tumor cells.

16 Claims, No Drawings

2-AMINO-6-ALKYL-5-(4-SUBSTITUTED-1-PIPERAZINYL) PYRIMIDIN-4-ONES, THE PREPARATION AND USE THEREOF

TECHNICAL FIELD OF THE INVENTION

The present invention relates to the therapeutical application of 2-Amino-6-alkyl-5-(4-Substituted-1-Piperazinyl) pyrimidin-4-ones derivatives.

BACKGROUND OF THE INVENTION

Background

Methotrexate (MTX), a dihydrofolate reductase inhibitor, has long been used as antitumor agent. However, problem of drug resistance emerged as one of its unfavorable characteristics. The acquired resistance is either due to the alteration of target enzymes or impaired carrier-mediated cellular uptake (Dixon et al, *J. Biol. Chem.*, 1994, 269, 17–20; Matherly et al, *J. Biol. Chem.* 1992, 267, 23253–23260). We reported a series of 2,4-diaminopyrimidines(1) as open-ring analogues of MTX for inhibition of dihydrofolate reductase. The introduction of pyrimidinyl moiety into the molecule in replacing the pteridine ring of MTX was thought to eliminate conformational rigidity and, in consequence, to enhance the accessibility of the molecules into the active site of the target enzyme. These compounds showed cytotoxicity on mice bearing murine leukemia P388, L1210 and sarcoma. Some of the compounds with high lipophilicity were active against WI-L2/MTX$^r$ MTX-resistant strain of cancer cells (Werbel et al, in *Chemistry and Biology of Pteridines*, ed. by Cooper, B. A. and Whitehead, V. M. Walter de Gruyter & Co. Berlin, 1986, 69–71). The resistance is due to an impaired cellular uptake mechanism. The open-ring analogues seemed to provide better lipophilicity and conformational flexability in regard to improving cellular uptake and accessibility to the target enzyme.

Recent reports revealed that 5,10-dideaza-5,6,7,8-tetrahydrofolic acid (DDATHF, known as lometrexol currently in clinical trial) is a potent inhibitor, of glycinamide ribonucleotide transformylase(GAR-Tfase) (Baldwin et al, *Biochemistry*, 1991, 30, 1997–2006), an enzyme in purine de novo biosynthesis which catalyzes one-carbon-unit transfer reaction using $N^5$, $N^{10}$-methenyltetrahydrofolic acid (MTHF) as a cofactor. Interest in this new target for antitumor agents and the difficulty in synthesis of DDATHF has led to the development of other pyrimidine compounds as open-chain analogues (Hodson et al, *J. Med. Chem.*, 1994, 37, 2112–2115; Harrington et al, *J. Med. Chem.*, 1992, 35, 1109–1116.). However, most of the open-chain analogues were not as active as DDATHF, possibly due to the high degree of conformational flexibility of the side chain moieties attached to the pyrimidine ring.

SIGNIFICANCE OF THE STUDY

In consideration of lipophilicity and structural flexibility, we designed and prepared a series of 2-amino-6-alkyl-5-(4-substituted-1-piperazinyl) pyrimidin-4(3H)-ones as open-ring analogues of MTHF (FIG. 1). The significance of structural design on these compounds is (1) being lipophilic (Allegra et al, *Antimicrob. Agents Chemother.* 1988, 32, 430–433.) for improvement of cellular uptake; (2) with 2-aminopyrimidin- 4(3H)-one skeleton and (3) using piperazine as a bridge to maintain four-atom distance from the pyrimidine ring to the phenyl ring so as to keep the molecules conformationally similar to that of MTHF.

DETAILED DESCRIPTION OF THE INVENTION

Summary of the Invention

A series of 2-amino-6-alkyl-5-(4-substituted-1-piperazinyl) pyrimidin-4(3H)-one were synthesized, which having the structural formula I where

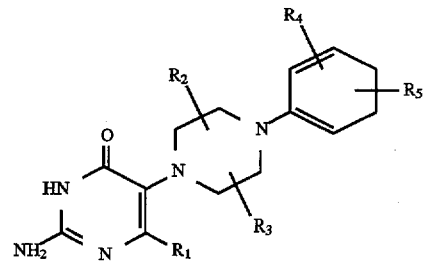

$R_1$ is hydrogen or alkyl of from one to six carbon atoms;

$R_2$ and $R_3$ are independently hydrogen or alkyl of from one to six carbon atoms, vinyl or acetylenic;

$R_4$ and $R_5$ are independently (1). hydrogen, halogen, nitro, cyano, trifluoromethyl, hydroxyl, alkyl of from one to six carbon atoms, alkoxyl of from one to six carbon atoms, or alkanoyl of from one to six carbon atoms;

(2). —$NR_6R_7$, where $R_6$ and $R_7$ are independently hydrogen, alkyl of from one to six carbon atoms, or alkanoyl of from one to six carbon atoms;

(3). —$COOR_8$, where $R_8$ is hydrogen, a pharmaceutically acceptable metal cation, a pharmaceutically acceptable amine cation, or alkyl of from one to six carbon atoms, (4). —$CONR_9R_{10}$ or $CONHNR_9R_{10}$ where $R_9$ and $R_{10}$ are independently hydrogen, alkyl of from one to six carbon atoms, alkyl of from one to six carbon atoms substituted with one or two carboxyl groups, alkyl of from one to six carbon atoms substituted with one or two carboxyl groups and one —OH, —SH, —NHC(=NH) $NH_2$, or —$NH_2$ group, alkyl of from one to six carbon atoms substituted with one or two alkoxycarbonyl groups of from one to six carbon atoms, or alkyl of from one to six carbon atoms substituted with one or two alkoxycarbonyl groups of from one to six carbon atoms and one —OH, NHC (=NH) $NH_2$, —SH, or —$NH_2$ group;

(5).

where $R_{11}$ is hydrogen, or alkyl of from one to six carbon atoms;

(6). —$SO_2R_{12}$, where $R_{12}$ is hydroxyl, alkyl of from one to six carbon atoms, alkoxy of from one to six carbon atoms or —$NR_{13} R_{14}$ where $R_{13}$ and $R_{14}$ are independently hydrogen or alkyl of from one to six carbon atoms or benzyl;

and the pharmaceutically acceptable salts thereof.

The preparation of the series of 2-amino-6-alkyl-5-(4-substituted-1-piperazinyl)pyrimidin-4-(3H)-ones were summerized in Scheme 1. Condensation of N-benzylpiperazine with ethyl 2-oxo-3-chloropropionate gave intermediate 3. Condensation of 3, with guanidine afforded intermediate 4. Debenzylation of 4 under hydrogen in the presence of palladium on charcoal gave compound 5. Coupling of compound 5 with 4-fluorobenzonitrile followed by hydrochloric acid treatment gave compound 7. Coupling of 7 with diethyl glutamate by which upon gave compound 8, saponification with methanolic sodium hydroxide gave product 9. Compounds 10–14 were prepared as analogues of 9 without the glutamate side chain. Analogue 10 was prepared by coupling intermediate 5 with 4-fluoronitrobenzene. Condensation of 5 with N,N-dibenzyl-4-fluorobenzene sulfonamide followed by debenzylation gave compound 12. Reduction of 6 by hydrogenation gave compound 13. Esterification of 7 gave compound 14. The structures of compound of formula I described above were assigned according to the IR, NMR, MS, and elemental analytical data.

Compounds were subjected to the disease-oriented antitumor screening on 60 cancer cell lines in the National Cancer Institute of the U.S.A. (Grever, M. R. et al., *Seminars in Oncology* 1992, 19, 622–638). Results of cytotoxicity are summarized in Table 1, $GI_{50}$ values represent the concentrations corresponding to 50% of growth inhibition. Interestingly, most of the compounds showed selective cytotoxicity for the SNB75 CNS cell line. The $GI_{50}$ for compounds 8, 9 and 10 are less than $10^{-8}$M.

This invention included the preparation of the antitumor agent. These active compounds, as free type or their pharmaceutically acceptable salts, may be administered parenterally or orally in a suitable pharmaceutical form. They also may be administered along or in conjunction with other selective cytotoxicity agents, in combination with any pharmaceutically acceptable carrier.

As used herein, the pharmaceutically acceptable salts include salts with inorganic acids, such as hydrochloride, hydrobromide, sulfate and phosphate; organic acids; after such as acetate, maleate, tartarate, and methanesulfonate; and with amino acids, such as arginine, aspartic acid and glutamic acid. Suitable pharmaceutical forms include sterile aqueous solutions or dispersions, sterile powders, tablets, troches, pills, capsules. In addition, the active compounds may be incorporated into sustained-release preparations and formulations. The pharmaceutically acceptable carrier includes any and all solvents, disintegrating agents, binders, excipients, lubricants, absorption delaying agents and the like. Although the compound of the present invention may also be present as a hydrate or as a stereoisomer, it is a matter of course that these hydrates and stereoisomers are also included in the scope of the present invention.

SIGNIFICANCE OF THE INVENTION

The significance of the invention is that these analogues are designed as lipophilic open-ring analogues for overcoming the problem of drug resistance commonly occurred on antifolates in resistant cancer cells due to impaired carrier-mediated cellular uptake. In addition, as open-ring analogues of $N^5$, $N^{10}$-methenyltetrahydrofolic acid(MTHF), the cofactor for GART fase and thymydylate synthetase along DNA de novo synthesis, these compounds are thought to eliminate conformational rigidity and, in consequence, to enhance the accessibility of the molecules into the active site of the target enzyme. Antitumor screening on disease-oriented human cancer cell lines indicated that compounds, 6, 8, 9, 10 and 12 showed selective cytotoxicity on human CNS tumor cell lines with growth inhibition ($GI_{50}$) ranged from $1\times10^{-7}$M to less than $10^{-8}$M.

Cancer cells have higher rate of purine de novo biosynthesis than normal cells. Inhibition on GAR-Tfase represents a new target for designing cytotoxic agents with selectivity on cancer cells. In this invention, structural modification on the GAR-Tfase cofactor MTHF has led to a series of 2-amino-6-methyl-5-(4-substituted-1-piperazinyl) pyrimidin-4-(3H)-ones. Brain minor specificity was noticed for this series of compounds. From the screening data released, five out of thirteen compounds tested showed selective cytotoxicity on human CNS tumor cell line. In comparison with the rigid structure of MTHF, the conformational flexibility of these open-ring analogues might count for their accessibility to the target enzyme.

DESCRIPTION OF THE FIGURES

Table 1. Cytotoxic activity of compounds 6–12 on human cancer cell lines.

FIG. 1. structure of MTHF, MTX, and target compounds

Scheme 1. method in preparation of the compounds with formula I

DESCRIPTION OF EXPERIMENTS

The new compounds can be prepared according to the following reaction schemes and protocols.

Example 1

Ethyl 2-(4-phenylmethylpiperazin-1-yl)-3-oxo-butyrate (3)

A mixture of ethyl 3-chloro-2-oxopropionate (85.15 g, 0.52 mol), N-benzylpiperazine (6.42 g, 0.49 mol) and $K_2CO_3$ (7.1 g, 0.52 mol) in 1L of AcCN was stirred at 50° C. for 24 h. AcCN was removed in vacuo. The residue was partitioned between aqueous $Na_2CO_3$ solution (5%, 300 mL) and EtOAC (300 mL×2). The combined EtOAc solution was extracted with 1N aqueous HCl solution. The aqueous solution was separated, neutralized with $Na_2CO_3$ to pH 9 and extracted with EtOAc (250 mL×2). The EtOAc layer was separated, dried over $MgSO_4$ and filtered. The filtrate was concentrated in vacuo to give 132.60 g (89%) of the desired product as pale yellow liquid. IR(KBr): 3011, 2940, 2810, 1740, 1720, 1650, 1358, 1325, 1250, 1016 cm$^{-1}$; $^1$H-NMR (80 MHz, CDCl$_3$): δ 1.17–1.24 (t, J=7.1 Hz, 3H, CH$_3$CH$_2$OCO—), 2.05 (s, 3H, CH$_3$CO—), 2.40–2.50 (m, 4H, piperazinyl-H), 2.60–2.70 (m, 4H, piperazinyl-H), 3.45 (s, 2H, —CH$_2$—Ph), 3.84 (s, 1H, CH$_3$CO—CH—), 4.11–4.18 (q, J=7.1 Hz, 2H, CH$_3$CH$_2$OCO—), 7.10–7.29 (m, 5H, Ph-H) ppm; EI MS m/z (relative-intensity): 304 (M$^+$, 13), 261 (100), 231 (10), 170 (29), 91 (95).

Example 2

2-Amino-6-methyl-5-(4-phenylmethylpiperazin-1-yl)pyrimidin-4(3H)-one (4)

Sodium (2.43 g, 0.11 mol) was dissolved in 2-methoxyethanol (150 mL). A 2- methoxyethanol solution (100 mL) containing compound 3 (30.40 g, 0.10 mol) and guanidine hydrochloride (10.03 g, 0.11 mol) was then added. The mixture was heated under reflux for 13 h. After the reaction, the solvent was removed in vacuo. The residue was triturated with 300 mL of water and the solid precipitate was collected. Recrystallization from 95% ethanol gave 17.54 g (59%) of the product as white solid. mp: 280°–281° C.; IR (KBr): 3350 (br), 3160, 3080, 2940, 2850, 1650, 1610, 1540, 1390 cm$^{-1}$; $^1$H-NMR(80 MHz, DMSO-d$_6$): δ 2.07(s, 3H, CH$_3$—), 2.25–2.65(m, 4H, piperazinyl-H), 2.75–3.10(m, 4H, piperazinyl-H), 5.9–6.4(brs, 2H, —NH$_2$), 7.0–7.4(m, 5H, Ph-H) ppm; EI MS m/z (relative intensity): 299 (M$^+$, 30), 208 (20), 180(10), 165(20), 153(53), 146 (19), 91 (100); Anal for C$_{16}$H$_{21}$N$_5$O.½ H$_2$O: Calcd. C, 62.32; H, 7.19; N, 22.71; Found C, 61.99; H, 7.34; N, 22.75.

Example 3

2-Amino-6-methyl-5-(4-piperazin-1-yl)pyrimidin-4(3H)-one(5)

A solution of compound 4 (16.56 g, 5.50 mmol) in glacial acetic acid (200 mL) was subjected to hydrogenolysis in the presence of 0.5 g of 10% Pd/C under 1 atm of hydrogen for 34 h. When the reaction was judged complete, the catalyst was removed by filtration and glacial acetic acid was removed in vacuo. The residue was triturated with dilute aqueous $Na_2CO_3$ solution to allow the solid to precipitate. The solid was collected and recrystallized from hot water to give, after drying in vacuo at 80° C. overnight, 10.67 g (92%) of the desired product as white needles. mp: 285°–286° C.; IR (KBr): 3350 (br), 3180, 2950, 2850, 1655, 1350, 1240 $cm^{-1}$; $^1$H-NMR (80 MHz, $D_2O+NaOH$): δ 2.59 (s, 3H, $CH_3$—), 3.05–3.50 (m, 8H, piperazinyl-H) ppm; EI MS m/z (relative intensity): 209 ($M^+$, 45), 167 (100), 153 (23); Anal for $C_9H_{15}N_5O$: Calcd. C, 49.53; H, 7.39; N, 32.09; Found C, 49.39; H, 7.55; N, 32.03.

Example 4

4-[4-(2-Amino-6-methyl-4(3H)-oxopyrimidin-5-yl)piperazin-1-yl]benzonitrile (6)

A mixture of compound 5 (8.70 g, 41.63 mmol), 4-fluorobenzonitrile (5.10 g, 42.15 mmol) and $K_2CO_3$ (6.89 g, 49.96 mmol) in DMF (250 mL) was heated under reflux for 7 h. DMF was removed in vacuo. The residue was triturated with water (250 mL) to facilitate precipitation. The recipitate was collected by filtration and recrystallized from DMF. After drying in vacuo at 80° C. overnight, 8.20 g (64%) of the product was obtained as white needles. mp: 330° C.(decp); IR (KBr): 3125, 2900, 2860, 2220, 1680, 1620, 1580, 1515, 1440, 1380, 1320, 1275, 1240, 1180, 1100, 1040 $cm^{-1}$; $^1$H-NMR(80 MHz, DMSO-$d_6$): δ 2.13 (s, 3H, $CH_3$—), 2.90–3.20 (m, 4H, piperazinyl-H), 3.21–3.50 (m, 4H, piperazinyl-H), 6.12–6.45 (brs, 2H, —$NH_2$), 6.85–7.15 & 7.40–7.70 (ABq, J=8.8 Hz, 4H, Ph-H) ppm; EI MS m/z (relative intensity): 310 ($M^+$, 100), 295 (48), 179 (15), 166 (13), 153 (97), 129 (30), 102 (25), 73(20); HRMS for $C_{16}H_{18}N_6O$ Calcd 310.1542; Found 310.1545.

Example 5

4-[4-(2-Amino-6-methyl-4(3H)-oxopyrimidin-5-yl)piperazin-1-yl]benzoic acid (7)

A solution of compound 6 (6.07 g, 19.40 mmol) in concentrated HCl solution (100 mL) was heated under reflux for 12 h. The solvent was removed in vacuo. The residue was triturated with ice water (100 mL) and the solid precipitate was collected by filtration. Recrystallized from DMF gave, after drying in vacuo at 80° C. overnight, 4.85 g (75%) of the product as white needles. mp: 295°–296° C. (decp); IR (KBr): 3400 (br), 3150, 2975, 2850, 1680, 1650, 1610, 1520, 1380, 1240, 1190 $cm^{-1}$; $^1$H-NMR (80 MHz, DMSO-$d_6$): δ 1.15–1.45 (t, J=7.04 Hz, 3H, $CH_3CH_2$—), 2.12 (s, 3H, —$CH_3$) 2.8–3.5 (m, 8H, piperazinyl-H), 4.05–4.45 (q, J=7.04 Hz, 2H, $CH_3CH_2$—), 6.15–6.45 (br, 2H, —$NH_2$), 6.80–7.15 & 7.40–7.70 (ABq, J=8.92 Hz, 4H, Ph-H) ppm; EI MS m/z (relative intensity): 357 ($M^+$, 35), 342 (35), 312 (11), 179 (21), 166 (20), 153 (100), 138 (10), 132 (25), 125 (21). RMS for $C_{16}H_{19}N_5O_3$: Calcd. 329.1487; Found 329.1492.

Example 6

Diethyl N-[4-[4-(2-Amino-6-methyl-4(3H)-oxo pyrimidin-5-yl)piperazin-1-yl]benzoyl] glutamic acid (8)

A solution of compound. 7 (3.29 g, 10.00 mmol), 1-ethyl-3-(3-dimethylaminopropyl)carbodiimide(EDCI, 2.11 g, 11.00 mmol), 1-hydroxybenzotriazole monohydrate (HOBt, 1.36 g, 10.00 mmol), diethyl glutamate hydrochloride (2.40 g, 10.00 mmol) and N-methyl morphorine (NMM, 2.11 g, 10.00 mmol) in DMF (150 mL) was stirred at 50° C. for 28 h. DMF was removed in vacuo. The residue was triturated subsequently with EtOAc and water by virtue of sonication to removed unreacted substances. The white precipitate was collected and recrystallized from 95% ethanol to give, after drying in vacuo at 80° C. overnight, 4.05 g (79%) of the desired product. mp: 290°–291° C.; IR (KBr): 3370 (br), 3150, 2980, 2850, 1738, 1730, 1660, 1640, 1610, 1510, 1230 $cm^{-1}$; $^1$H-NMR (400 MHz, DMSO-$d_6$): δ 1.1–1.2 (m, 6H, 2$CH_3CH_2$—), 1.9–2.0 (m, 2H, —$CH_2CH_2COOEt$), 2.1 (s, 3H, $CH_3$), 2.4 (m, 2H, —$CH_2COOEt$), 2.9–3.5 (m, 8H, piperazinyl-H), 4.0–4.1 (m, 4H, 2$CH_3CH_2$—), 4.4–4.5 (m, 1H, —CONHCH), 6.3 (s, 2H, $NH_2$), 6.9 & 7.7 (ABq, J=8.8 Hz, 4H, Ph-H), 8.3 (d, J=7.6 Hz, 1H, —CONH), 10.6 (s, 1H, pyrimidine NH) ppm; EI MS m/z (relative intensity): 514 ($M^+$, 10), 499 (31), 391 (10), 362 (1.0), 349 (30), 340 (25), 312 (55), 283 (7), 189 (21), 179(31), 160(30), 153 (100), 141 (65), 84 (80); HRMS for $C_{25}H_{34}N_6O_6$: Calcd. 514.2539; Found 514.2535.

Example 7

N-[4-[4-(2-Amino-6-methyl-4-(3H)-oxopyrimidin-5-yl)piperazin-1-yl]benzoyl]glutamic acid (9)

A solution of 8 (2.16 g, 4.20 mmol) in 3N NaOH (30 mL) was stirred at rt for 7 h. The mixture was acidified with 1N HCl solution. The solid was collected by filtration and recrystallized with a mixture of water and DMF to give, after drying in vacuo at 80° C. overnight, 1.63 g (85%) of the desired product. mp: 265°–266° C.; IR (KBr): 3320, 2944, 2815, 1704, 1659, 1606, 1510, 1231 $cm^{-1}$; $^1$H-NMR (400 MHz, DMSO-$d_6$): δ 1.95–2.05 (m, 2H, $CH_3CH_2CH_2$—), 2.12 (s, 3H, $CH_3$—), 2.30–2.36 (t, J=7.4 Hz, 2H, $CH_3CH_2CH_2$—), 2.85–3.5 (m, 8H, piperazinyl-H), 4.33–4.46 (td, J=7.4 Hz, 7.68 Hz, 1H, —NHCH—), 6.29 (brs, 2H, —$NH_2$), 6.90–7.00 & 7.74–7.80 (ABq, J=8.84 Hz, 4H, Ph-H), 8.20–8.30 (d, J=7.68 Hz, 1H, —CONH); EI MS m/z (relative intensity): 458 ($M^+$, 70), 424 (65), 407 (70), 361 (100).

Example 8

2-Amino-6-methyl-5-[4-(4-nitrophenyl)piperazin-1-yl]pyrimidin-4(3H)-one (10)

A mixture of compound 5 (1.00 g, 4.78 mmol), 4-fluoronitrobenzene (0.67 g, 4.78 mmol) and $K_2CO_3$ (0.66 g, 4.78 mol) in EtOH (50 mL) was heated under reflux for 11 h. DMF was removed in vacuo. The residue was washed with 50 mL of EtOAc to removed the soluble reactants and filtered. The solid residue was then triturated with 50 mL of water. Recrystallized from DMF to give 1.21 g (77%) of the product as white needles. mp: 330° C.(decp); IR (KBr): 3350 (br), 3150, 2825, 2740, 1660, 1630, 1590, 1490, 1390, 1100 $cm^{-1}$; $^1$H-NMR (80 MHz, DMSO-$d_6$): δ 2.13 (s, 3H, $CH_3$—), 2.90–3.20 (m,4H, piperazinyl-H), 3.40–3.70 (m, 4H, piperazinyl-H), 6.00–6.50 (brs, 2H, —$NH_2$), 6.85–7.2 &

7.89–8.2 (ABq, J=9.36 Hz, 4H, Ph-H) ppm; EI MS m/z (relative intensity): 330 (M$^+$, 85), 315 (45), 179 (20), 166 (18), 153 (100), 125 (25), 73(20); HRMS. for $C_{15}H_{18}O_3N_6$: Calcd. 330.1440; Found 330.1443.

Example 9

N,N-Dibenzyl 4-[4-(2-amino-6-methyl-4-OH)-oxopyrimidin-5-yl)piperazin-1-yl]-benzenesulfonamide (11)

A mixture of compound 5 (2.09 g, 10.00 mmol), N,N-dibenzyl 4-fluorobenzenesulfonamide (3.55 g, 10.00 mmol) and $K_2CO_3$ (1.52 g, 11.00 mmol) in 25 mL of DMSO was heated under reflux for 9 h. DMSO was removed in vacuo. The residue was triturated with 100 mL of ice water to facilitate precipitation. The solid was collected and recrystallized from 2-methoxyethynal to give, after drying in vacuo at 80° C. overnight, 3.41 g (63%) of the product as off white solid. mp: 289°–290° C.; IR (KBr): 3400 (br), 3150 (br), 3060, 2920, 2850, 1670, 1650, 1640, 1590, 1510, 1315, 1307, 1150 cm$^{-1}$; $^1$H-NMR (80 MHz, DMSO-d$_6$): δ 2.14 (s, 3H, CH$_3$—), 2.89–3.19(m,4H, piperazinyl-H), 3.20–3.40 (m, 4H, piperazinyl-H), 4.22 (s, 4H, —CH$_2$—Ph), 6.15–6.41 (brs, 2H, —NH$_2$), 6.9–7.8 (m, 14H, Ph-H) ppm; EI MS m/z (relative intensity): 544 (M$^+$, 20), 529 (85), 421 (80), 379 (100), 153 (35), 91 (65); Anal for $C_{29}H_{32}N_6O_3S$: Calcd. C, 63.95; H, 5.92; N, 15.43; Found C, 63.60; H, 5.91; N, 15.20.

Example 10

4-[4-(2-Amino-6-methyl-4-(3H)-oxopyrimidin-5-yl)-piperazin-1-yl]benzenesulfonamide (12)

A solution of compound 11 (1.36 g, 2.50 mmol) in 20 mL of ice-cold concentrated sulfuric acid was allowed to stirred at rt for 7.5 h. After the reaction, the mixture was poured onto 50 mL of ice and then partitioned with 50 mL of EtOAc. The aqueous layer was isolated, neutralized with 6N NaOH solution. The precipitate was collected and washed with water. Recrystallization from DMF afford 0.83 g (91%) of the desired product as white solid. mp: 300° C.(decp) IR (KBr): 3436, 2750 (br), 1651, 1596, 1117, 1110 cm$^{-1}$; $^1$H-NMR (80MHz, DMSO-d$_6$): δ 2.12 (s, 3H, CH$_3$), 3.9–3.5 (m, 8H, piperazinyl-H), 6.27 (s, 2H, NH$_2$), 6.9–7.2 (m, 4H, Ph-H, SO$_2$NH$_2$), 7.4–7.7 (d, 2H, J=8.2 Hz, Ph-H) ppm; EI MS m/z (relative intensity): 364 (M$^+$, 20), 349 (50), 153 (100). HRMS for $C_{15}H_{20}N_6O_3S$: Calcd. 364.1317: Found 364.1313.

Example 11

2-Amino-5-[4-(4-aminomethylphenyl)-piperazin-1-yl]-6-methylpyrimidine-4-(3H)-one (13)

A solution of compound 6 (0.10 g, 0.32 mmol) and 0.5 mL of hydrochloric acid in 20 mL of EtOH was subjected to hydrogenolysis in the presence of 0.03 g of 10% Pd/C under 3.5 atm of hydrogen for 50 h. When the reaction was judged complete, the catalyst was removed by filtration and the solvent was evaporated in vacuo. The residue was triturated with dilute aqueous Na$_2$CO$_3$ solution to allow precipitation. The solid was collected and recrystallized from 95% EtOH to give, after drying in vacuo at 80° C. overnight, 82.0 mg (81%) of the desired product as white powder. mp: 281°–282.5° C. (decp); IR (KBr): 3435, 3145, 2918, 1651, 1558, 1517 cm$^{-1}$; $^1$H-NMR (80 MHz, D$_2$O+TFA): δ 1.99 (s, 3H, CH$_3$—), 2.90–3.50(m, 8H, piperazinyl-H), 3.86 (s, 2H, —CH$_2$ NH$_2$), 7.1–7.4 (m, 4H, Ph-H) ppm; EI MS m/z (relative intensity): 314 (M$^+$, 52), 299 (90), 179 (21), 166 (30), 153(100), 133 (52), 125 (40), 118 (30), 106 (42), 77(20); HRMS for $C_{16}H_{22}N_6O$: Calcd. 314.1855; Found: 314.1850.

Example 12

4-[4-(2-Amino-6-methyl-4-(3H)-oxopyrimidin-5-yl)-piperazin-1-yl]benzoic acid ethyl ester (14)

A mixture of compound 7 (0.30 g 0.91 mmol) and 1.0 mL of sulfuric acid in 50 mL of 95% EtOH was heated under reflux for 22 h. EtOH was removed in vacuo. The residue was poured onto 100 mL of ice water and neutralized with concentrated Na$_2$CO$_3$ solution. The precipitate was collected and washed with 50 mL of water. Recrystallized from 95% EtOH afforded, after drying in vacuo at 80° C. overnight, 4.05 g (79%) of the product as white powder. mp: 330° C. (decp), mp: 290°–291° C.; IR (KBr): 3400 (br), 3180 (br), 2980, 2840, 1680, 1650, 1610, 1510, 1380, 1330, 1275, 1235, 1190, 1160 cm$^{-1}$; $^1$H-NMR (80 MHz, DMSO-d$_6$): δ 2.15 (s, 3H, CH$_3$—), 2.80–3.60 (m, 8H, piperazinyl-H), 6.40–6.78 (brs, 2H, —NH$_2$), 6.80–7.10 (d, 2H, J=8.84 Hz, Ph-H), 7.60–7.90 (d, 2H, J=8.84 Hz, Ph-H) ppm; HRMS m/z for $C_{18}H_{23}N_5O_3$: Calcd. 357.1800; Found: 357.1802.

Example 13

A typical tablet which may be prepared by conventional tableting techniques with the following composition:

| | |
|---|---|
| active compound | 50 mg |
| lactose | 30 mg |
| starch | 4 mg |
| mag.stearate | 6 mg |
| corn starch | 10 mg |
| to make total of | 100 mg |

TABLE 1

Cytotoxic activity of compounds 6-12 on human cancer cell lines.

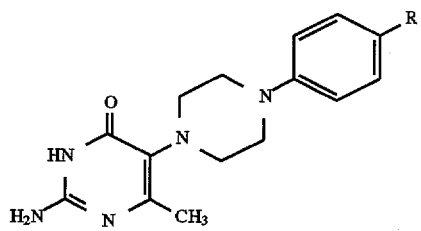

| compound | R | \multicolumn{7}{c|}{Cytotoxic activity($GI_{50}$, $\mu M$)[a]} |
|---|---|---|---|---|---|---|---|---|
| | | lung | colon | CNS | ovarian | renal | prostate | breast |
| 6 | —CN | —[b] | — | 0.04[c] | 93 | — | — | — |
| 7 | —COOH | — | — | — | — | 1.39 | — | — |
| 8 | —CONH—CH—($CH_2$)$_2$COOEt<br>            \|<br>          COOEt | — | — | <0.01[c] | — | — | — | — |
| 9 | —CONH—CH—($CH_2$)$_2$COOH<br>            \|<br>          COOH | — | — | <0.01[c] | — | — | — | — |
| 10 | —$NO_2$ | — | — | <0.01[c] | — | — | — | — |
| 11 | $SO_2N(CH_2Ph)_2$ | 4.8–79 | 55 | 3.68[d] | 0.7–16 | 3.1–27 | 1.9–3.5 | 2.1–37 |
| 12 | $SO_2NH_2$ | — | — | 0.10[c] | — | — | — | — |

[a] The value represents the range of $GI_{50}$'s for the cell lines of each respective cancer unless specified.
[b] — denotes $GI_{50} > 10^{-4}$ M.
[c] CNS SNB-75 cell line.
[d] CNS U251 cell line.

FIG. 1

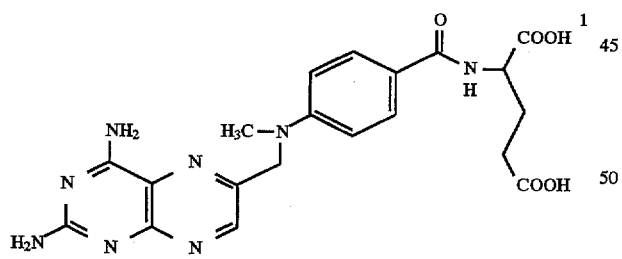

1

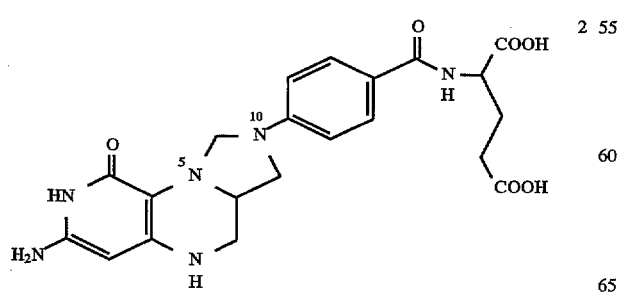

2

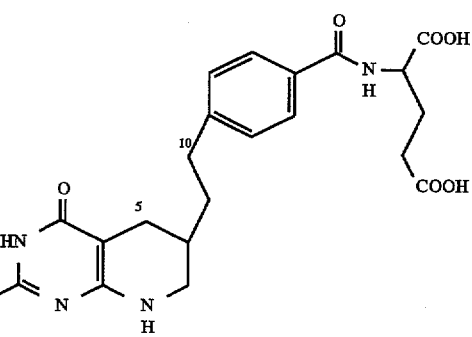

3

-continued
FIG. 1

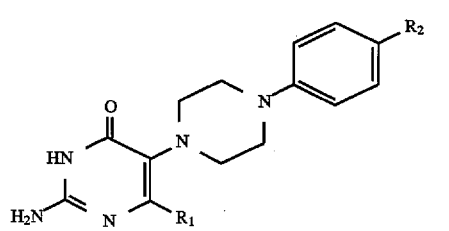

4

Scheme 1
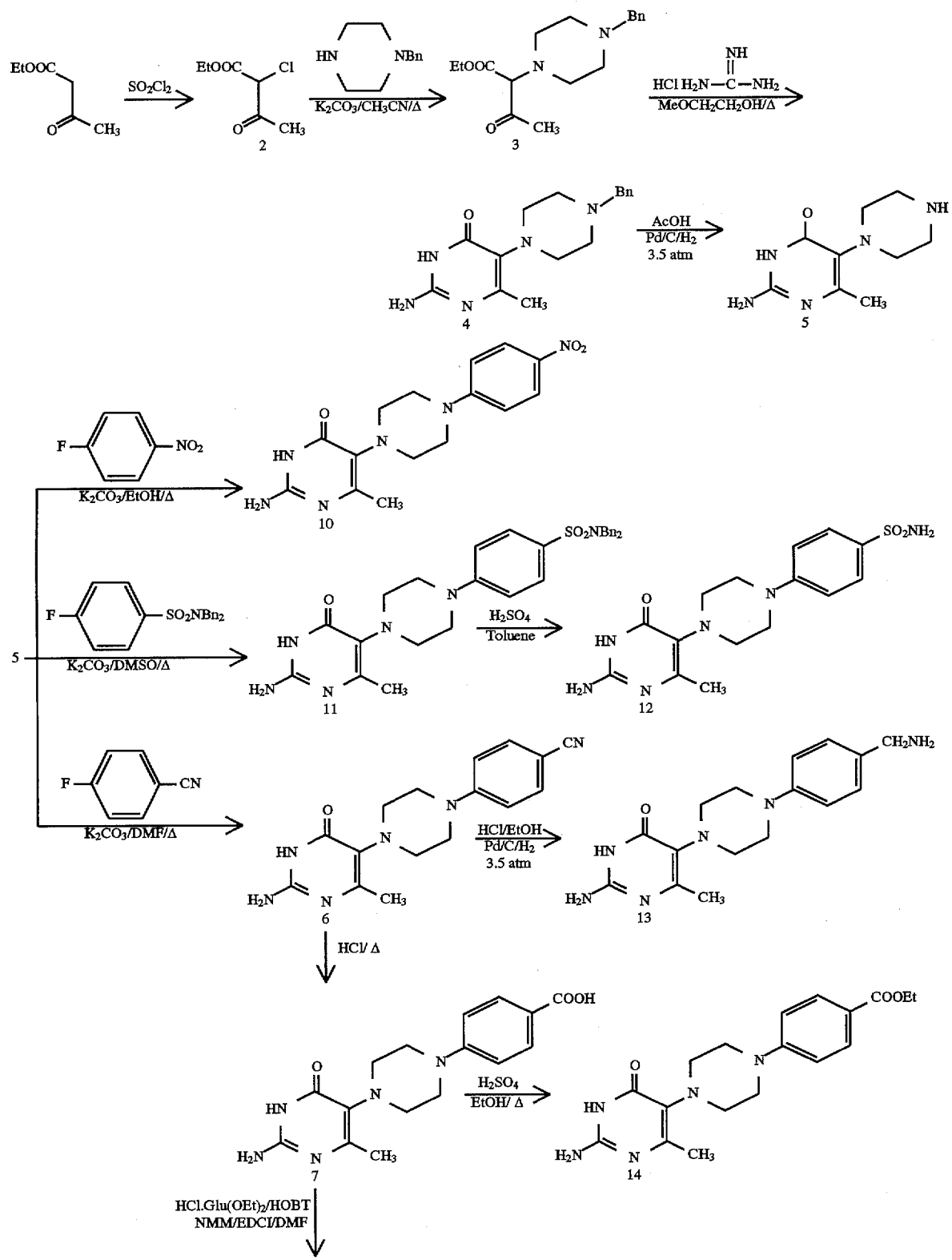

-continued
Scheme 1

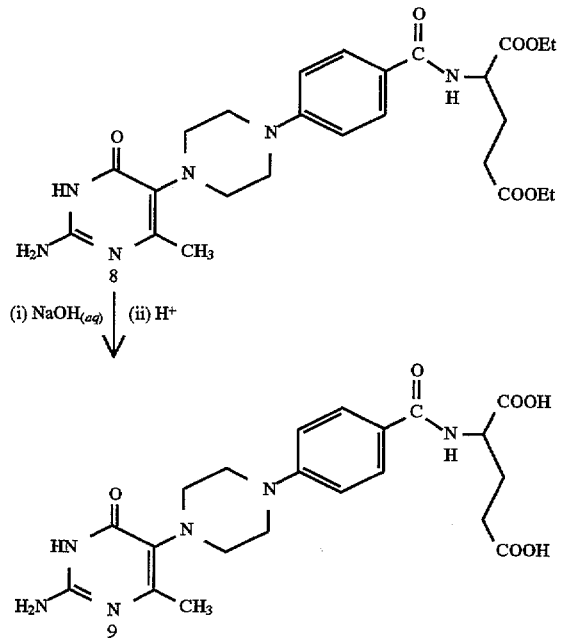

We claim:
1. A compound having the structural formula I where

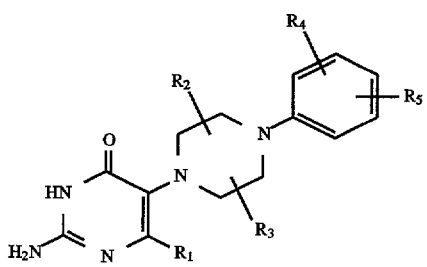

$R_1$ is hydrogen or alkyl of from one to six carbon atoms;
$R_2$ and $R_3$ are independently hydrogen or alkyl of from one to six carbon atoms, vinyl or acetylenyl;
$R_4$ and $R_5$ are independently
(1). hydrogen, halogen, nitro, cyano, trifluoromethyl, hydroxyl, alkyl of from one to six carbon atoms, alkoxyl of from one to six carbon atoms, or alkanoyl of from one to six carbon atoms;
(2). —$NR_6R_7$, where $R_6$ and $R_7$ are independently hydrogen, alkyl of from one to six carbon atoms, or alkanoyl of from one to six carbon atoms;
(3). —$COOR_8$, where $R_8$ is hydrogen, a pharmaceutically acceptable metal cation, a pharmaceutically acceptable amine cation, or alkyl of from one to six carbon atoms;
(5).

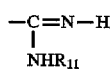

where $R_{11}$ is hydrogen, or alkyl of from one to six carbon atoms;
(6). —$SO_2R_{12}$, where $R_{12}$ is hydroxyl, alkyl of from one to six carbon atoms, alkoxy of from one to six carbon atoms or —$NR_{13}R_{14}$ where $R_{13}$ and $R_{14}$ are independently hydrogen or alkyl of from one to six carbon atoms or benzyl;

and the pharmaceutically acceptable salts thereof.
2. The compound of claim 1, wherein $R_4$ and $R_5$ are independently
(1). nitro, cyano, trifluoromethyl, or alkanoyl of from one to six carbon atoms;
(2). —$COOR_8$, where $R_8$ is hydrogen, a pharmaceutically acceptable metal cation, a pharmaceutically acceptable amine cation, or alkyl of from one to six carbon atoms;
(4).

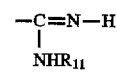

where $R_{11}$ is hydrogen, or alkyl of from one to six carbon atoms;
(5). —$SO_2R_{12}$, where $R_{12}$ is hydroxyl, alkyl of from one to six carbon atoms, alkoxy of from one to six carbon atoms, or —$NR_{13}R_{14}$ where $R_{13}$ and $R_{14}$ are independently hydrogen or alkyl of from one to six carbon atoms or benzyl;
and the pharmaceutically acceptable salts thereof.
3. A pharmaceutical composition comprising a compound of claim 1 or a pharmaceutically acceptable salt thereof in combination with a pharmaceutically acceptable carrier.
4. A method of producing a compound having structural formula I

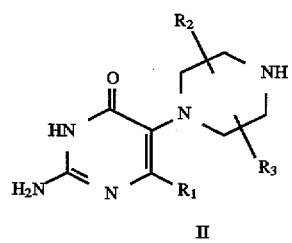

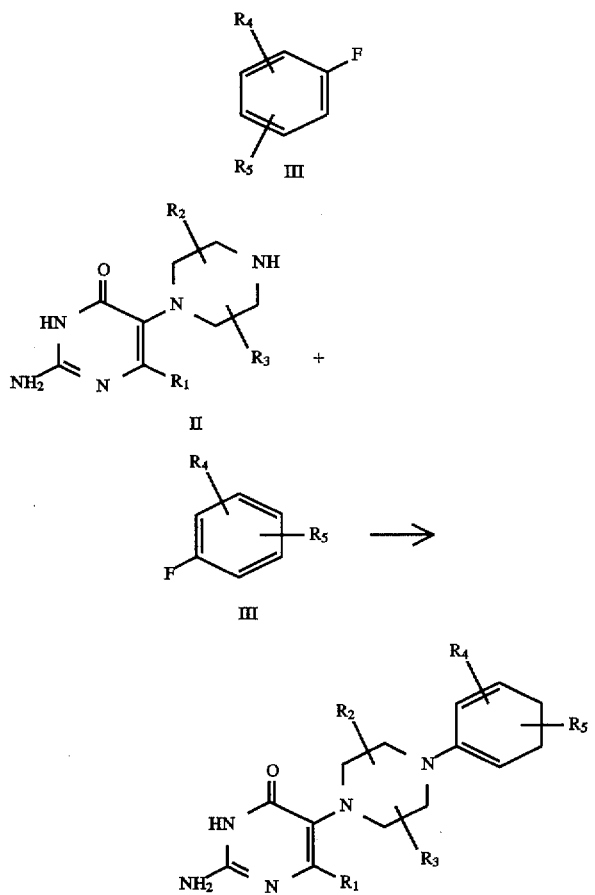

of claim 1 wherein $R_1$, $R_2$, $R_3$, $R_4$, and $R_5$ are as defined in claim 1, by reacting a compound having formula II with a substituted fluorophenyl compound of structural formula III, in a polar organic solvent in the presence of a base, and further converting said compound of structural formula I, if desired, to a pharmaceutically acceptable salt.

5. A compound having structural formula II of claim 4 wherein R1, R2, and R3 are as defined in claim 4.

6. A method for treating human brain tumor by administering an effective amount of a pharmaceutical composition of claim 3.

7. The compound of claim 1, wherein $R_4$ and $R_5$ are independently (1) hydrogen, halogen, nitro, cyano, trifluoromethyl, hydroxyl, alkyl of from one to six carbon atoms, alkoxyl of from one to six carbon atoms, or alkanoyl of from one to six carbon atoms;

(2) —$NR_6R_7$, wherein $R_6$ and $R_7$ are independently hydrogen, alkyl of from one to six carbon atoms, or alkanoyl of from one to six carbon atoms;

(3) —$COOR_8$, wherein $R_8$ is hydrogen, a pharmaceutically acceptable metal cation, a pharmaceutically acceptable amine cation, or alkyl of from one to six carbon atoms;

(4)

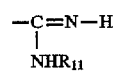

wherein $R_{11}$ is hydrogen, or alkyl of from one to six carbon atoms;

and the pharmaceutically acceptable salts thereof.

8. The compound of claim 2, wherein $R_4$ and $R_5$ are independently (1) nitro, cyano, trifluoromethyl, or alkanoyl of from one to six carbon atoms;

(2) —$COOR_8$, where $R_8$ is hydrogen, a pharmaceutically acceptable metal cation, a pharmaceutically acceptable amine cation, or alkyl of from one to six carbon atoms;

(3)

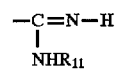

where $R_{11}$ is hydrogen, or alkyl of from one to six carbon atoms;

and the pharmaceutically acceptable salts thereof.

9. The compound of claim 7, wherein $R_4$ and $R_5$ are independently (1) hydrogen, halogen, nitro, cyano, trifluoromethyl, hydroxyl, alkyl of from one to six carbon atoms, alkoxyl of from one to six carbon atoms, or alkanoyl of from one to six carbon atoms;

(2) —$NR_6R_7$, wherein $R_6$ and $R_7$ are independently hydrogen, alkyl of from one to six carbon atoms, or alkanoyl of from one to six carbon atoms;

(3)

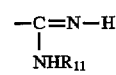

wherein $R_{11}$ is hydrogen, or alkyl of from one to six carbon atoms;

and the pharmaceutically acceptable salts thereof.

10. The compound of claim 8, wherein $R_4$ and $R_5$ are independently (1) nitro, cyano, trifluoromethyl, or alkanoyl of from one to six carbon atoms;

(2)

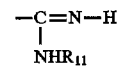

where $R_{11}$ is hydrogen, or alkyl of from one to six carbon atoms;

and the pharmaceutically acceptable salts thereof.

11. The compound of claim 1, wherein $R_1$ is —$CH_3$;

$R_2$ and $R_3$ are —H;

$R_4$ is at the para position and is —CN, —NO$_2$, or —SO$_2$NH$_2$; and $R_5$ is —H at a non-para position.

12. A method for treating human brain tumor, said method comprising administering to said tumor a pharmaceutical composition comprising a compound of claim 7 or a salt thereof.

13. A method for treating human brain tumor, said method comprising administering to said tumor a pharmaceutical composition comprising a compound of claim 8 or a salt thereof.

14. A method for treating human brain tumor, said method comprising administering to said tumor a pharmaceutical composition comprising a compound of claim 9 or a salt thereof.

15. A method for treating human brain tumor, said method comprising administering to said tumor a pharmaceutical composition comprising a compound of claim 10 or a salt thereof.

16. A method for treating human brain tumor, said method comprising administering to said tumor a pharmaceutical composition comprising a compound of claim 11 or a salt thereof.

* * * * *